United States Patent [19]

Kesling

[11] Patent Number: 4,907,966

[45] Date of Patent: Mar. 13, 1990

[54] IMPRESSION TRAY FOR RETENTION OF IMPRESSION MATERIAL

[75] Inventor: Christopher K. Kesling, LaPorte, Ind.

[73] Assignee: TP Orthodontics, Inc., Westville, Ind.

[21] Appl. No.: 350,317

[22] Filed: May 11, 1989

[51] Int. Cl.⁴ .............................................. A61C 9/00
[52] U.S. Cl. ........................................ 433/37; 433/38
[58] Field of Search ....................... 433/37, 38, 41, 42, 433/43, 44, 45, 46, 47

[56] References Cited

U.S. PATENT DOCUMENTS

| | | | |
|---|---|---|---|
| 2,597,929 | 5/1952 | Gorsky et al. | 433/37 |
| 2,848,811 | 8/1958 | Wagner | 433/38 |
| 2,963,786 | 12/1960 | Browning | 433/37 |
| 3,534,475 | 10/1970 | St. Hilaire | 433/37 |
| 3,686,759 | 8/1972 | Pross geb. Hogreve | 433/37 |
| 3,834,025 | 9/1974 | Schunemann | 433/37 |
| 4,003,132 | 1/1977 | Beck | 433/42 |
| 4,146,963 | 4/1979 | Schreinemakers | 433/37 |
| 4,227,877 | 10/1980 | Tureaud et al. | 433/37 |
| 4,368,040 | 1/1983 | Weissman | 433/37 |
| 4,530,662 | 7/1985 | Andersson et al. | 433/37 |

Primary Examiner—John J. Wilson
Attorney, Agent, or Firm—Lloyd L. Zickert

[57] ABSTRACT

A dental impression tray of substantially rigid material having impression material retention means for enhancing the retention of the impression material to the tray during the removal of the tray/impression material from the mouth after taking of an impression and for facilitating the removal and cleaning of the impression material from the tray after the impression has been recorded wherein the retaining means includes one or more elastomeric members stretched between anchoring points and positioned to be enveloped by the impression material loaded into the tray.

10 Claims, 2 Drawing Sheets

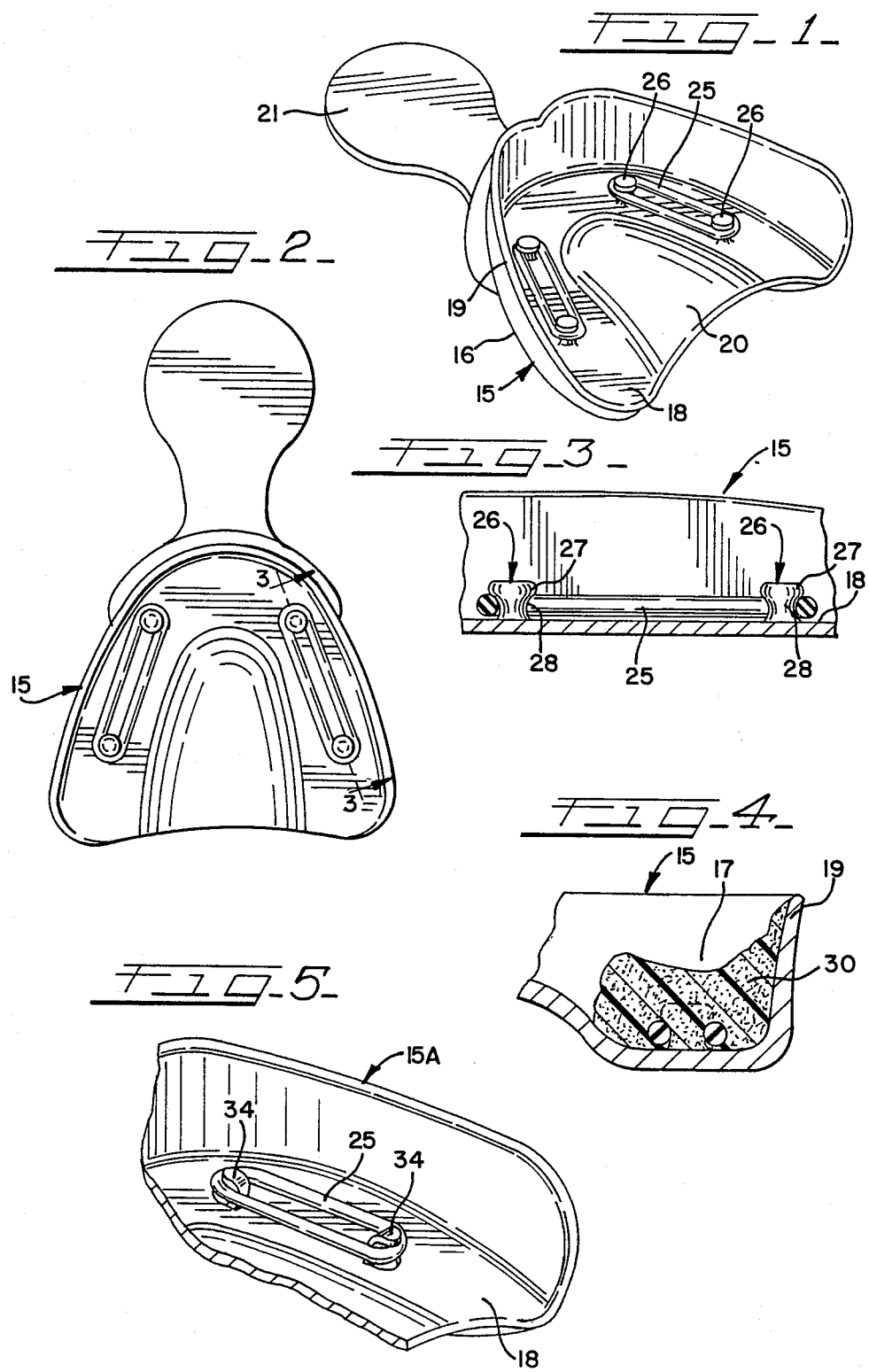

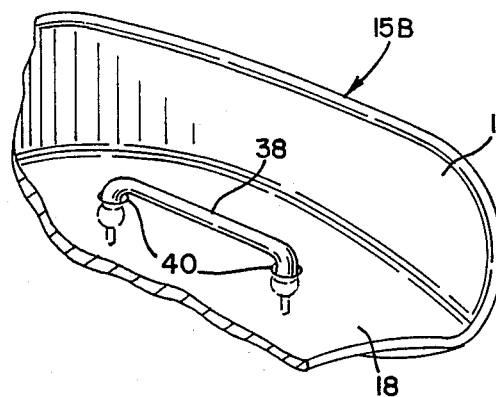
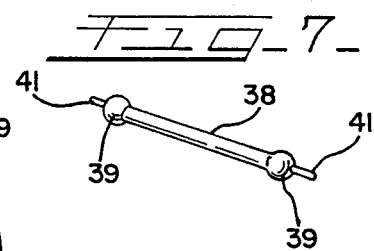
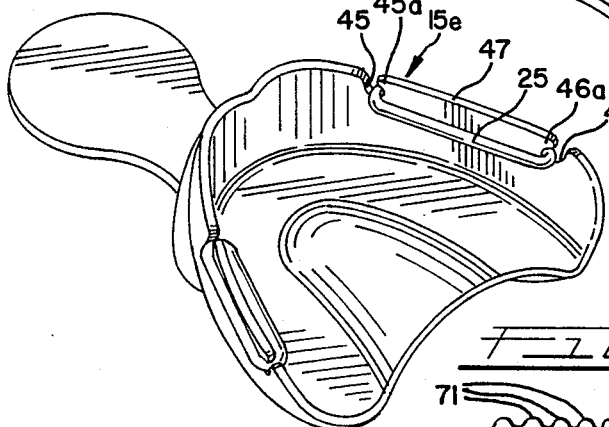
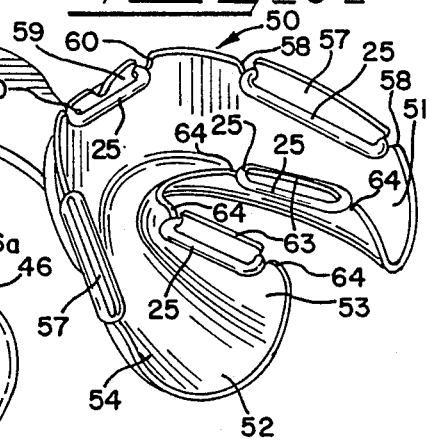
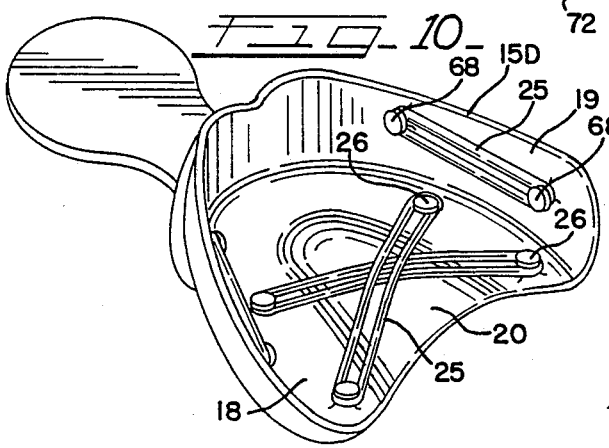
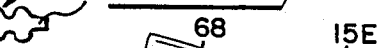
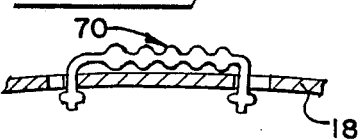

IMPRESSION TRAY FOR RETENTION OF IMPRESSION MATERIAL

DESCRIPTION

This invention relates in general to an impression tray and more particularly to an impression tray having means for increasing the retention of impression material so as to inhibit separation of the impression material from the tray during the removal of the tray/impression material from the mouth of the patient and still more particularly to the retention means in the form of elastomeric elements anchored to the tray in stretched form.

BACKGROUND OF THE INVENTION

Impression trays are used by dentists for purposes of making impressions of the teeth and adjacent tissue so that custom-made prosthetics and appliances can be made for a patient such as for restorative dental work or orthodontic treatment. The steps included for making the impression include the loading of an impression tray with impression material sufficient to obtain the desired impression and then taking the impression by inserting the tray/impression material into the mouth of a patent and having it engage the teeth and tissue for which an impression is desired. The impression material is allowed to set and then the tray/impression material is removed from the patient's mouth followed by a recording of that impression such as by pouring and curing a suitable plaster or stone in the impression. If during the removal of the tray/impression material from the mouth of a patient the impression material becomes substantially disengaged from the tray the impression taken may be sufficiently destroyed or distorted thereby necessitating the taking of a further impression.

Various devices have been heretofore developed for assisting in the retention of impression material in the impression tray to inhibit separation of the impression material from the tray during the removal of the tray-/impression material from the mouth of a patient. These devices have included perforations or apertures in the form of round holes and wires as in U.S. Pat. No. 2,963,786; extending arms terminating in ball-shaped ends as in U.S. Pat. No. 3,686,759; enlarged flanged edges and ribs as seen in U.S. Pat. No. 3,834,025; a plurality of slits as seen in U.S. Pat. No. 4,146,963; upwardly extending ball-shaped members as seen in U.S. Pat. No. 4,227,877; undercuts as seen in U.S. Pat. No. 4,368,040; and non-woven fabric bonded to the surface receiving the impression material as seen in U.S. Pat. No. 4,530,662. Various other methods of retention have also been used, many of which have resulted in presenting difficulty in cleaning the trays for future use once the impression has been recorded.

SUMMARY OF THE INVENTION

The impression tray retention means of the present invention not only serves to greatly enhance the retention of the impression material in the tray when the tray/impression material is removed from the mouth of a patient but also functions to facilitate the cleaning of the impression tray once the impression has been recorded. The retention means of the present invention includes anchoring elements for stretching elastomeric members that contact and are essentially surrounded by the impression material once the impression material is loaded into the tray. The anchoring elements may take various forms such as buttons secured to the tray in spaced relation or hooks formed on the tray. Additionally, the anchoring means may take other forms such as holes formed in the tray or notches formed along the flanges of the tray. The elastomeric members may be in the form of rubber bands or stranded members which would be positioned in the tray so that they could be surrounded by the impression material loaded into the tray.

The elastomeric members would be first placed in stretched form on the tray and thereafter the impression material would be loaded into the tray. Following the recording of an impression made by the material, it will be appreciated that separation of the material from the tray can be accomplished by exerting extra force on the impression material to separate it from the tray and where the elastomeric members may be easily removed with the impression material or the impression material would separate from the elastomers. Thus, the essential means used for enhancing the retention of the impression material in the tray is easily separable from the tray during cleaning. This contrasts with heretofore known retention means which remain with the tray and thereby make cleaning more difficult. Elastomeric retention devices were not previously known.

It is therefore an object of the present invention to provide a new and improved retention means for a dental impression tray for retaining the impression material in the tray during the taking of an impression and removing the impression material from the mouth of the patient and therefore facilitating the cleaning of the tray for use in taking a further impression.

A still further object of the present invention is in the provision of an improved retention means for a dental impression tray that not only serves to enhance the retention of the impression material in the tray during removal of the tray/impression material from the mouth of the patient but also facilitates the cleaning of the tray once the impression has been recorded inasmuch as the retention means essentially separates from the tray during cleaning.

Another object of the present invention is in the provision of a retention means for an impression tray to enhance the retention of the impression material in the tray when removing the tray/impression material from the mouth of a patient and which is in the form of anchoring means on the tray and elastomeric members stretched on the anchoring means and which ultimately constitutes substantially the entire retention means.

Other objects, features and advantages of the invention will be apparent from the following detailed disclosure, taken in conjunction with the accompanying sheets of drawings, wherein like reference numerals refer to like parts.

BRIEF DESCRIPTION OF THE DRAWINGS

FIG. 1 is a perspective view of a dental impression tray having one form of the retention means of the present invention;

FIG. 2 is a top plan view of the embodiment of FIG. 1;

FIG. 3 is a sectional view taken substantially along line 3—3 of FIG. 2;

FIG. 4 is a sectional view taken through the retention means in the embodiment of FIGS. 1-3 and also illustrating the manner in which the elastomeric member is enveloped by the impression material when the impression material is loaded in the tray;

FIG. 5 is a fragmentary perspective view of another form of the invention wherein the anchoring means is in the form of hooks;

FIG. 6 is a view similar to FIG. 5 illustrating another form of the retention means wherein the anchoring means is in the form of holes in the tray and the elastomeric means is in the form of a strand having enlarged ends;

FIG. 7 is a perspective view of the elastomeric member in FIG. 6 when in relaxed form;

FIG. 8 is a perspective view of a still further embodiment wherein the anchoring means for an endless elastomeric member is in the form of notches defining a post along the outer flange of a tray used to take an impression of the upper jaw;

FIG. 9 is a perspective view of a tray used for taking an impression of the lower jaw and illustrating the type of retention means shown in FIG. 8 wherein elastomeric members are mounted on both the inner and outer flanges of the tray;

FIG. 10 is a perspective view of the still further embodiment of the invention illustrating the use of the elastomeric members anchored to the side wall or flange of the tray as well as across the bottom of a tray used for taking an impression of the upper jaw;

FIG. 11 is a fragmentary perspective view showing a still further embodiment of the invention wherein the anchoring means is in the form of key-shaped holes in the tray and the elastomeric member is in the form of a strand having a plurality of spaced enlargements therealong;

FIG. 12 is a sectional view taken substantially along 12—12 of FIG. 11 illustrating the disposition of the elastomeric member; and FIG. 13 is a view of the elastomeric member shown in the embodiment of FIGS. 11 and 12 before it is mounted on the tray.

DESCRIPTION OF THE INVENTION

Referring now to the drawings it will be seen that impression trays illustrated include both a tray for taking impression of the upper jaw as well as a tray for the impression of the lower jaw. Several variations of the invention are illustrated although each retention mean is in the form of stretched elastomeric member that would be engaged by the impression material loaded into the tray.

Referring now to the embodiment of FIGS. 1 to 4 the tray illustrated is one for taking an impression of the upper jaw and generally indicated by the numeral 15. The tray includes a body 16 having a cavity 17 defined by a bottom wall 18, an upstanding outer flange or side wall 19 and a central palate portion 20. The cavity 17 is horse-shoe shaped in the form of an arch of a jaw. At the front end of the tray a handle or tongue 21 is provided for manipulating the tray by the person taking the impression.

The retention means of the invention in this embodiment is mounted on the bottom 18 of the tray although it will be appreciated that it may be mounted along the inside surface of the side wall or flange 19 as shown in FIG. 10. Also the retention means is provided on each side of the tray and is in the form of an elastomeric member 25 stretched to cover a substantial portion of the bottom at each side. The elastomeric member 25 is in the form of a continuous band such as a rubber band which may take the form of an o-ring or oval in relaxed form and it is stretched between anchoring pins or buttons 26 that are secured to the bottom of the tray in any suitable manner. The endless band as shown is of uniform cross section throughout, but may even have spaced enlargements therealong. While the elastomeric member is shown as an endless band, it may take the form of an elastomeric chain.

Preferably as seen in FIG. 3 the anchoring pins 26 include a head portion 27 and a reduced in size stem 28 so that once the continuous elastomeric band 25 is mounted on the pins the head portions 27 will inhibit removal of the band upon application of a force thereto. It will also be appreciated that the reduced stem portion 28 has a concave in cross section shape which automatically spaces the elastomeric member slightly above the bottom 18 and as seen in FIG. 4 when the tray is loaded with impression material, the impression material will substantially surround and envelop the band 25. The impression material is designated by the numeral 30 in FIG. 4 and may be of any suitable type depending upon the type of impression taken, the impression material will be either loaded to the top edge of the flange 19 or even slightly over the edge depending on the type used.

While a tray 15 is illustrated as no having any perforations it will be appreciated that perforations may be provided if desired which would still further enhance the retention of an impression material. Further, the tray may be made of any suitable substantially rigid material such as metal or plastic and if made of metal may be provided with a coating of Teflon or the like.

Another form of anchoring element for elastomeric bands is shown in FIG. 5 with the tray being generally designated as 15A. This tray differs only in that hooks 34 extend from the bottom 18 around which the endless elastomeric member 25 may be trained in stretched form. The hooks are shown as being punched out of the bottom but may be individual parts suitably mounted on the bottom of the tray. This form is merely shown to illustrate other types of anchoring elements mounted on the tray for anchoring the endless elastomeric band.

Another form of retention means according to the invention is illustrated in FIG. 6 for the same type of tray as shown in FIG. 1 and which includes an elastomeric member in the form of a strand 38 having enlarged ends 39 which may be in the shape of a ball or otherwise. The strand 38 is anchored to the tray by providing holes 40 formed in the bottom 18 of a size slightly smaller than the enlarged ends of the strand whereby the ends may be forced into and through the holes 40 and thereby locked in place with the strand 38 in stretched form. Again, this strand arrangement may be used on the bottom of the tray or on the side wall 19 or in both places. It will be appreciated that the strand will serve in the same fashion as the endless band except that it will only provide a single strand while the endless band provides double strands between the anchoring means. Additionally, it will be appreciated that the strand will be surrounded or enveloped by the impression material when the impression material is loaded into the tray. Tails 41 may be formed integral with the elastomeric member and which extend from the enlarged ends which can be gripped by a tool to assist in pulling the enlarged heads 39 through the holes 40 in the tray.

Another version of the present invention is shown in FIG. 8 wherein the tray is identified by the numeral 15C and is of the same type as shown in FIG. 1 for use in taking an upper impression. The retention device for this embodiment is mounted on the upper edge of the outer flange or side wall by notching the side wall at spaced points 45 and 46 to define therebetween an elongated post 47 over which the endless elastomeric member 25 is stretched. Each of the notches 45 and 46 are formed so that at opposite ends of the post 47 hooked portions 45A and 46A are formed so as to positively engage the stretched elastic member once it is applied to the post. Here a post is provided on opposite sides of the tray along the flange and it will be appreciated that any number of posts may be formed along the flange for purposes of receiving a stretched elastomeric member. It may be further appreciated that the elastomeric member 25 will, by virtue of the post 27 being on the flange edge, dispose a strand on the inner surface of the flange as well as on the outer surface of the flange so that runover of the impression material will be gripped on both sides of the flange.

Another illustration of the present invention is shown in FIG. 9 in connection with an impression tray 50 which is formed for use in taking an impression of the lower jaw and having an open center and therefore being completely horseshoe shaped to define a trough or cavity 51 which is in turn defined by a bottom wall 52, and upstanding inner and outer flanges or side walls 53 and 54. This embodiment utilizes essentially the same type of retention means as illustrated in FIG. 8 except that the retention means can be provided on both the inner and outer side walls or flanges. On the outer flanges 54 elongated posts 57 are defined by notches 58 of the same type as shown in the embodiment of FIG. 8 and around which elastomeric bands 25 are trained. Additionally, a forward or front post 59 is defined by notches 60 for retaining the stretched elastomeric band 25 at the front of the flange 54. Thus, three elastomeric bands are mounted on the outer flange of the impression tray and it can be appreciated that the same number could be utilized on a tray of the type shown in FIG. 8. Additionally, elongated posts 63 are defined by notches 64 on the inner flange or side wall 53 for receiving stretched elastomeric bands 25 and providing retention means on the inner side wall of the impression tray. Again, it will be appreciated that the impression material will not only have retention on the inside of the flanges but also on the outside of the flanges as the impression material runs over the top edges of the flanges.

The embodiment of FIG. 10 where the tray is generally designated 15D inasmuch as it is the same type of tray as in FIG. 1 with the exception of the type of retention means illustrated which differs from the embodiment of FIG. 1 only in that buttons or pins are mounted on the inside of the outer flange for mounting of elastomeric bands and also the arrangement of the bands that are at the bottom of the tray is a little different. More specifically, the inner side wall 19 of the tray includes at each side pins or buttons 68 of the same type that is shown in the embodiment of FIG. 1 and over which an elastomeric band 25 may be stretched to mount a retaining elastomeric band on the inside wall of the flange to provide additional retention. Further the pins 26 mounted in the bottom 18, while in the same positions as the pins in the embodiment of FIG. 1, are shown to have cross elastic bands connected over the palate portion 20 rather than having the elastic bands running along the bottom of the tray cavity. In this respect, retention is provided in the center of the tray as well as a part of the bottom wall and also then along the inner side walls of the tray.

A further version of the invention is illustrated in FIG. 11 with the tray 15E and where the tray is of the same type as shown in FIGS. 1, 6, 8 and 10. This embodiment differs from the embodiment of FIG. 6 in that spaced key-hole shaped openings 68 are provided in the bottom 18 of the tray for anchoring opposite ends of an elastomeric strand 70. The strand 70 includes a plurality of spaced apart circular enlargements 71 interconnected by links or filaments 72 and having at opposite ends tails 73 to facilitate handling. As seen in FIG. 12 stretching of the strand 70 is accomplished so that the end-most enlargement 71 can be inserted into the keyhole opening 68 and then locked in place to disclose the remaining enlargements along the top surface of the bottom 18 thereby spacing the connecting links 72 from the top surface of the bottom 18 for allowing impression material to freely flow between the enlargements and underneath the links to enhance retention of the impression material in the tray.

Common to all of the embodiments are anchoring means on the tray for receiving in stretched form an elastomeric member whether it be an endless member or a strand member. Prior to use of the tray and loading of the impression material the strands are placed in position to provide the unique retention function. Once the impression material is loaded it will then coact with the retention means in order to assist in retaining the impression material in the tray and from becoming distorted when the tray/impression material is removed from the mouth of a patient. Thereafter, when the impression is recorded the tray may be easily cleaned by the removal of the impression material and which may also at the same time include the elastomeric members which may be disposable. Thereafter, the tray could be reloaded again and again with elastomeric members and impression material to make further impressions. However, the elastomeric members may be made with a life for repeated use, in which case the impression material would be separable from the elastomer. Cleaning of the elastomer in any suitable manner may be accomplished before reuse.

While certain retention elements are illustrated with certain trays, it should be understood that they may be mixed on one tray or used alternatively on any tray.

It will be understood that modifications and variations may be effected without departing from the scope of the novel concepts of the present invention, but it is understood that this application is to be limited only by the scope of the appended claims.

I claim:

1. A dental impression tray comprising a body of substantially rigid material shaped like the jaw of a person, said body including a cavity for receiving impression material, said cavity being defined by a bottom and upstanding outer flange means, and means for retaining impression material in the cavity during separation of the material from the mouth, said means including spaced anchoring means on the body and at least one elastomeric member stretched on the anchoring means to be engaged by the impression material to inhibit separation of the impression material from the tray when removing the tray/impression material from the mouth after the taking of an impression while thereafter facilitating removal of used impression material from the tray and cleaning of the tray following the recording of the impression.

2. The tray of claim 1, wherein said anchoring means includes at least one pair of spaced apart buttons secured to said body in the cavity, and said elastomeric member being in the form of an endless band trained over said buttons.

3. The tray of claim 2, wherein said anchoring means includes at least one pair of spaced apart hooks secured to said body in the cavity, and said elastomeric member being in the form of an endless band trained over said hooks.

4. The tray of claim 2, wherein said anchoring means includes at least one pair of spaced apart holes in the body within the cavity, and said elastomeric member is in the form of a strand having enlarged ends insertable through said holes and catching on the holes.

5. The tray of claim 4, wherein enlargements are provided along the strand to space the strand from the body.

6. The tray of claim 5, wherein said spaced apart holes are in said bottom of said body.

7. The tray of claim 5, wherein said holes are keyhole shaped.

8. The tray of claim 2, wherein said anchoring means includes at least one pair of spaced apart hooks along the flange means, and said elastomeric member being in the form of an endless band trained over said hooks.

9. The tray of claim 2, wherein said anchoring means includes at least one pair of spaced apart notches along the flange means defining an elongated post, and said elastomeric member being in the form of an endless band trained over said post.

10. The tray of claim 1, wherein the cavity is further defined by inner flange means, and said anchoring means includes at least one pair of spaced apart notches along each of said flange means defining opposed elongated posts, and said elastomer member being in the form of an endless band and one band being trained over each said post.

* * * * *

UNITED STATES PATENT AND TRADEMARK OFFICE
CERTIFICATE OF CORRECTION

PATENT NO. : 4,907,966
DATED : March 13, 1990
INVENTOR(S) : CHRISTOPHER K. KESLING It is certified that error appears in the above-identified patent and that said Letters Patent is hereby corrected as shown below:

```
Col. 1, line 24, change "patent" to --patient--;
Col. 4, line 19, after "type" insert a period (.) and
                 change "depending" to --Depending--;
        line 23, change "no" to --not--;
Col. 6, line 37, before "life" insert --long--.
```

Signed and Sealed this

Ninth Day of April, 1991

Attest:

HARRY F. MANBECK, JR.

Attesting Officer

Commissioner of Patents and Trademarks